United States Patent
Park et al.

(10) Patent No.: US 9,857,302 B2
(45) Date of Patent: Jan. 2, 2018

(54) METHOD AND APPARATUS FOR MANIPULATING NEAR FIELD USING LIGHT SCATTERING

(71) Applicant: Korea Advanced Institute of Science and Technology, Daejeon (KR)

(72) Inventors: Yongkeun Park, Seoul (KR); Jung-Hoon Park, Seoul (KR); Yong-Hoon Cho, Daejeon (KR); Chunghyun Park, Chungcheongbuk-do (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 15/009,608

(22) Filed: Jan. 28, 2016

(65) Prior Publication Data

US 2016/0146731 A1    May 26, 2016

Related U.S. Application Data

(62) Division of application No. 14/137,967, filed on Dec. 20, 2013, now Pat. No. 9,279,764.

(30) Foreign Application Priority Data

Jun. 26, 2013 (KR) .................. 10-2013-0073954
Oct. 17, 2013 (KR) .................. 10-2013-0123823

(51) Int. Cl.
*G01N 21/45* (2006.01)
*G01N 21/49* (2006.01)
(Continued)

(52) U.S. Cl.
CPC ......... *G01N 21/4788* (2013.01); *G01N 21/49* (2013.01); *G01Q 60/18* (2013.01);
(Continued)

(58) Field of Classification Search
None
See application file for complete search history.

(56) References Cited

U.S. PATENT DOCUMENTS 3,661,465 A * 5/1972 Groh .................. G01B 11/00
356/139.03
5,212,379 A * 5/1993 Nafarrate ............... A61B 5/113
250/227.14

(Continued)

FOREIGN PATENT DOCUMENTS

JP     2012-132886 A     7/2012

OTHER PUBLICATIONS

Park et al., Subwavelength light focusing using random nanoparticles, Nat. Photon. (Apr. 28, 2013).
(Continued)

*Primary Examiner* — Tri Ton
*Assistant Examiner* — Jarreas C Underwood
(74) *Attorney, Agent, or Firm* — Marshall, Gerstein & Borun LLP (57) ABSTRACT

An apparatus for manipulating surface near-field light resulting from light emitted from a light source that passes through a scattering layer is disclosed. Also, a method of finding a phase of incident light to cause constructive interference at a target spot using light scattering to manipulate the surface near-field.

9 Claims, 11 Drawing Sheets

(51) Int. Cl.
*G01Q 60/18* (2010.01)
*G01N 21/47* (2006.01)
*G01Q 60/22* (2010.01)

(52) U.S. Cl.
CPC ............ *G01Q 60/22* (2013.01); *G01N 21/45* (2013.01); *G01N 2021/479* (2013.01); *G01N 2201/0675* (2013.01)

(56) References Cited

U.S. PATENT DOCUMENTS

| | | | | |
|---|---|---|---|---|
| 5,636,014 A * | 6/1997 | Hanson | ...................... | G01P 3/36 324/175 |
| 5,739,527 A * | 4/1998 | Hecht | ...................... | B82Y 20/00 250/216 |
| 6,563,782 B1 * | 5/2003 | Oumi | ...................... | B82Y 10/00 369/126 |
| 6,587,426 B1 * | 7/2003 | Oumi | ...................... | B82Y 10/00 369/275.3 |
| 6,649,894 B2 * | 11/2003 | Matsumoto | ............ | B82Y 20/00 250/201.3 |
| 6,794,096 B2 * | 9/2004 | Kroyan | ...................... | G03F 1/30 430/5 |
| 6,949,732 B2 * | 9/2005 | Kiguchi | ................. | B82Y 20/00 250/216 |
| 7,336,372 B2 * | 2/2008 | Rosen | ...................... | G02B 27/48 356/515 |
| 7,449,688 B2 * | 11/2008 | Lewis | ...................... | B82Y 15/00 250/307 |
| 7,719,762 B2 * | 5/2010 | Kumasawa | .......... | G03B 21/604 359/449 |
| 7,928,900 B2 * | 4/2011 | Fuller | ...................... | G01S 7/414 342/175 |
| 7,969,650 B2 * | 6/2011 | Marks | ...................... | B82Y 20/00 359/363 |
| 8,045,253 B2 * | 10/2011 | Li | ............................. | G01D 5/30 356/521 |
| 8,552,402 B2 * | 10/2013 | Ye | ...................... | G01N 21/6458 250/459.1 |
| 8,587,474 B2 * | 11/2013 | Fuller | ...................... | G01S 7/414 342/11 |

OTHER PUBLICATIONS van Putten et al., "Scattering Lens Resolves sub-100 nm Structures with Visible Light," Complex Photonic Systems, Faculty of Science and Technology and MESA+ Institute for Nanotechnology, University of Twente, The Netherlands, University of Florence, Sesto Fiorentino, Italy and FOM Institute for Atomic and Molecular Physics, the Netherlands, Mar. 21, 2011.

* cited by examiner

METHOD AND APPARATUS FOR MANIPULATING NEAR FIELD USING LIGHT SCATTERING

BACKGROUND

Field of the Invention

The present invention relates to an optical field, and more particularly, to a method and an apparatus for forming a high-resolution optical focus and realizing near-field imaging.

Description of the Related Art

Traditional optical technology may not manipulate a near field essential to form an ultrahigh-resolution image or focus due to unique characteristics of light such as refraction and scattering, because it does not break diffraction limits according to Abbe's Law only with a conventional microscope and an object lens. A near field decays exponentially with distance as light is diffracted, and accordingly a near-field scanning optical microscope (NSOM) is developed due to limits of conventional equipment. NSOM technology for inspection of a sample with an about one hundred-nanometer opening for passage of light has many problems. Since the opening needs to physically come in direct contact with the sample to be measured, the technology is available to only for limited samples. Moreover, as the opening of an NSOM tip becomes smaller, a mode for passage of light disappears, and thus effective transmission of the light is impossible. In addition, light emitted from an ultra-small light source for measurement may be distorted by the NSOM tip, and an entire area of the sample to be measured is scanned with the NSOM tip, making it impossible to realize imaging in real time. To overcome these problems, a new area of plasmonics is recently on the rise. In plasmonics, however, a surface design is essential between a special metal and a dielectric, and a location of an ultrahigh-resolution focus is fixed by a manufacture material. Furthermore, the NSOM has a severe limit that an impractical increase in incident light is needed so as to obtain higher resolution, in addition to requiring that the small-size opening naturally and physically reach a target spot.

Nanotechnology currently on the rise is realized in two ways, which are divided into a bottom-up method using chemical synthesis and a top-down method using patterning such as lithography. Chemical synthesis may produce limited structures and is still not appropriate for constructing nano-devices widely used in the modern society, that is, electronic circuits. On the contrary, patterning such as lithography enables manufacture of large-area nanostructures and is in use for manufacturing various electronic chips for enabling the information society.

However, technology of manufacturing electronic circuits as one of ground forces for the modern society faces a huge obstacle that optical lithography used for nano-patterning is under the Abbe's diffraction limit. To overcome the obstacle, a smaller wavelength of light, that is, ultraviolet rays, is used, but due to increasing production costs and absence of scalability of the technology, a new technique is absolutely needed at this time.

SUMMARY

An aspect of the present invention is to form an ultrahigh-resolution image or focus by manipulating spatial distribution of light passing through a random scattering layer using light scattering.

Another aspect of the present invention is also to provide an apparatus and a method of manipulating a near field enabling ultrahigh-resolution imaging and lithography in a visible spectrum by forming an ultrahigh-resolution focus on a target sample disposed in an inside or a rear side of a scattering layer with a predetermined thickness.

Still another aspect of the present invention is to enable real-time imaging in a visible spectrum by allowing light emitted from a sample to be imaged to pass through a scattering layer so that a near field reaches a detector at a long distance.

According to an aspect of the present invention, there is provided an apparatus for manipulating a near field including a wavefront modulator, a scattering layer and a measuring layer. The wavefront modulator may manipulate a phase of light from a coherent light source. The scattering layer may pass the light with the manipulated phase. The measuring unit may measure a near field on a surface that the light passing through the scattering layer exits from.

The measuring unit may measure intensity of the light in a region smaller than an Abbe's diffraction limit in the near field.

The apparatus may form an ultrahigh-resolution focus on a target sample disposed in an inside or a rear side of the scattering layer.

The wavefront modulator may include a device for manipulating the phase of the light or a film with a fixed shape capable of manipulating the phase. For example, the wavefront modulator may include one of a spatial light modulator, a deformable mirror device, a dynamic mirror device, a photorefractive material and a holographic phase film.

The measuring unit may include an instrument using an opening or probe capable of measuring a smaller size of light than the Abbe's diffraction limit. For example, the measuring unit may include an NSOM, a structure having an opening with a smaller size than a diffraction limit, a light emitter having a smaller size than the diffraction limit or a probe having a vertex with a smaller size than the Abbe's diffraction limit.

The light source may include electromagnetic waves in all range including a visible-spectrum light source.

According to another aspect of the present invention, there is provided a method of manipulating a near field including manipulating a phase of light from a coherent light source using a wavefront modulator, passing the light with the manipulated phase through a scattering layer, and measuring a near field on a surface that the light passing through the scattering layer exits from.

The method may further include changing the phase of the light by adjusting the wavefront modulator based on a result of the measuring of the near field.

The changing of the phase of the light may include examining a phase in which constructive interference occurs while changing the phase of the light by adjusting the wavefront modulator, and recording the phase in which the constructive interference occurs.

The changing of the phase of the light may include changing the phase of the light until an ultrahigh-resolution focus is formed on a desired location.

Here, the wavefront modulator may include a device for manipulating the phase of the light or a film with a fixed shape capable of manipulating the phase. For example, the wavefront modulator may include one of a spatial light modulator, a deformable mirror device, a dynamic mirror device, a photorefractive material and a holographic phase film.

The light source may include electromagnetic waves in all range including a visible-spectrum light source.

According to still another aspect of the present invention, there is provided a near-field imaging apparatus including a light source, a scattering layer, a measuring unit to acquire speckle information on the scattering layer, and an analysis unit to analyze the speckle information. Here, the measuring unit may include a holographic measuring unit to acquire a phase of a speckle.

According to yet another aspect of the present invention, there is provided a method of realizing near-field imaging using a scattering layer involved in measuring scattering information. The method may include acquiring first speckle information on a speckle generated by light from a coherent light source passing through a scattering layer, acquiring second speckle information on a speckle generated by a plane wave passing through a sample and the scattering layer, and acquiring an image of the sample using the first speckle information and the second speckle information. Here, the acquiring of the first speckle information may include forming light of an input basis by passing the light from the coherent light source through a structure, passing the light of the input basis through the scattering layer to be scattered, and acquiring input basis speckle information on a speckle generated by the scattered light.

As described above, an apparatus and a method of manipulating a near field using light scattering according to an aspect of the present invention may manipulate a near field on a surface that the light passing through a scattering layer exits from using a wavefront modulator and the scattering layer.

Once information on an incident wavefront with respect to target spots is stored, ultrahigh-resolution optical focuses may be simultaneously formed at different spots or moved by adjusting the incident wavefront in real time.

Spatial frequency components derived from a near field around a target spot after passing through a scattering layer may include components beyond the Abbe's diffraction limit.

An apparatus and a method of manipulating a near field using light scattering according to an aspect of the present invention may use a light source having all range of wavelengths including a visible spectrum.

Lithography equipment including two devices only, a scattering layer and a wavefront modulator, may be manufactured.

An apparatus and a method of manipulating a near field using light scattering according to an aspect of the present invention may manipulate a nano-size optical focus.

A near-field imaging apparatus and method using light scattering according to an aspect of the present invention enables near-field imaging in a range of visible light which does not affect vital activities of living cells.

A nano-size optical focus or optical pattern generated by a near-field imaging apparatus and method using light scattering according to an aspect of the present invention may be used for optical tweezers or optical manipulation to capture an object optically.

A near-field imaging apparatus and method using light scattering according to an aspect of the present invention may realize large-size ultrahigh-resolution imaging of a sample in real time.

A near-field imaging apparatus and method using light scattering according to an aspect of the present invention enables dynamic observations of living cells.

A near-field imaging apparatus and method using light scattering according to an aspect of the present invention enables observations of even information on a near field with a general far-field optical microscope by converting the near field into a far field including a plurality of spatial frequencies.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Hereinafter, exemplary embodiments will be described in detail with reference to the accompanying drawings. A method of manipulating a near field using light scattering according to an exemplary embodiment will be carried out by an apparatus for manipulating a near field using light scattering.

Figure 1:
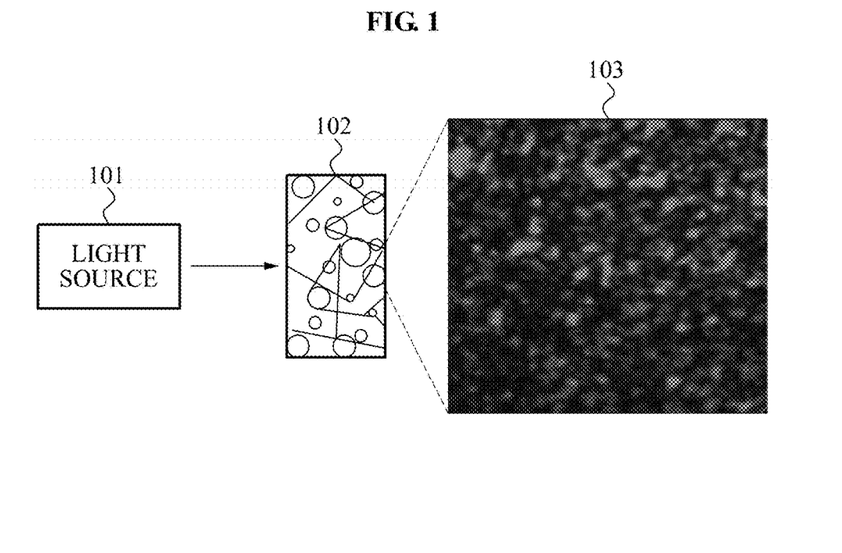
FIG. 1 illustrates problems resulting from light scattering.

FIG. 1 illustrates problems resulting from light scattering.

When light emitted from a light source 101 passes through a severely scattering material 102, a path and phase of the light change at random whenever the light meets scattering particles of the material 102. Particularly, in irregular distribution of fine particles, the Tyndall phenomenon occurs and a portion of the light traveling in straight lines decays in a path thereof. Here, when a coherent light source 101 such as a laser is used, a spot pattern including speckles 103 appears on a finally scattering surface. Such a phenomenon happens by constructive and offset interferences between lights having different phases according to scattering paths as the coherent light source meets the scattering particles of the severely scattering material 102. Such scattering makes it difficult for a conventional optical system to form an ultrahigh-resolution optical focus on a desired location.

Figure 2:
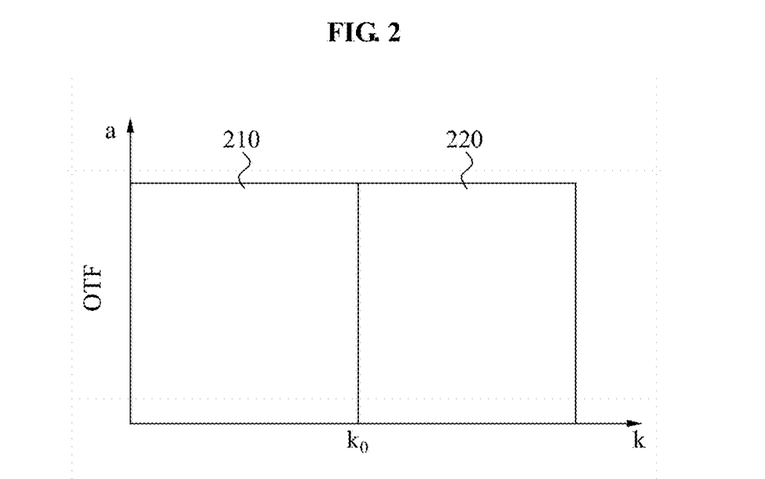
FIG. 2 is a graph illustrating problems of a conventional optical system.

FIG. 2 is a graph illustrating problems of a conventional optical system.

In FIG. 2, an x-axis denotes a spatial frequency and a y-axis denotes an optical transfer function. The conventional optical system may manipulate only a spatial frequency component within a maximum spatial frequency k0 determined by the optical transfer function thereof. For example, the conventional optical system may manipulate only a spatial frequency component 210 lower than the maximum spatial frequency k0. For |k|>|k0|, where k0 is the wave vector in free space, the wave vectors are evanescent and are consequently inaccessible in the far field using conventional optics. It is noticeable in a scattering process that even though light having a specific spatial frequency value enters a scattering layer first, resulting spatial frequency components of the light spread in an entire spatial frequency space. One exemplary embodiment may adjust a low spatial frequency component of incident light using scattering, thereby manipulating a high spatial frequency component of light, which is not modulated by the conventional optical system.

Figure 3A:
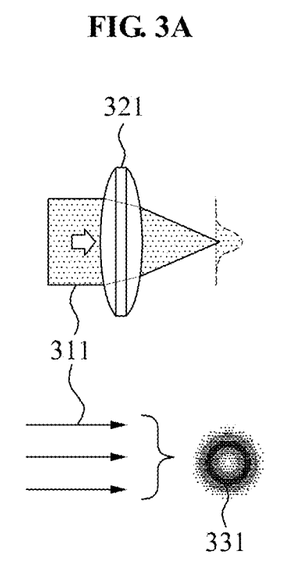
FIGS. 3A to 3C illustrate differences between the conventional optical system and an optical system according to an exemplary embodiment of the present invention.
Figure 3B:
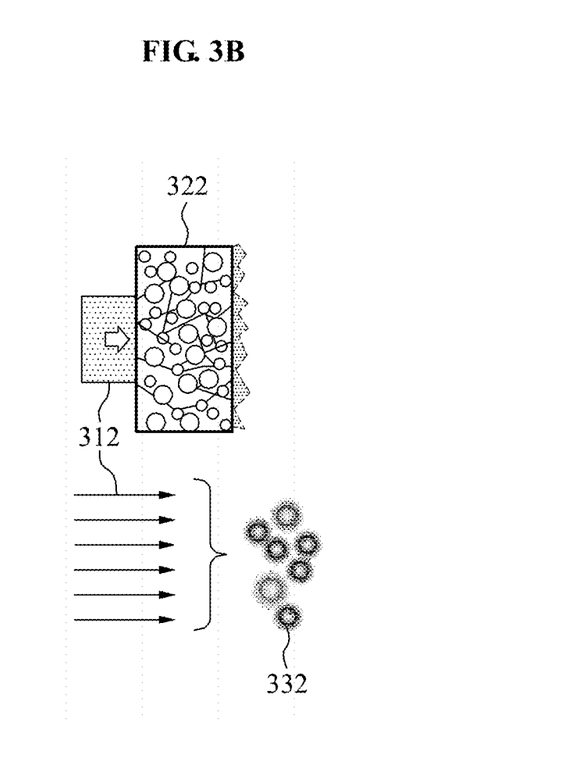
Figure 3C:
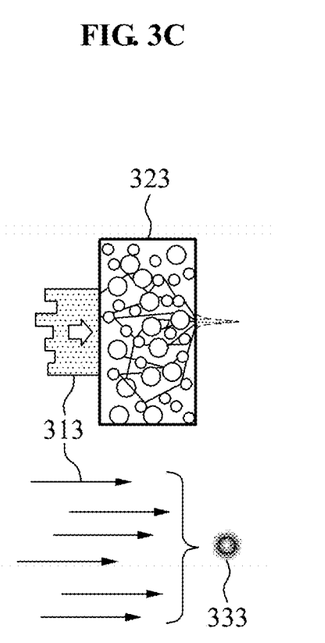

FIGS. 3A to 3C illustrate differences between the conventional optical system and an optical system according to an exemplary embodiment of the present invention.

Referring to FIG. 3A, the conventional optical system does not overcome an Abbe's diffraction limit and thus faces constraint in forming a smallest focus. According to Abbe's Law, resolution d of an optical microscope is proportional to a wavelength λ of light, represented by Equation 1.

$$d = \frac{0.61 * \lambda}{n * \sin\alpha} \quad [\text{Equation 1}]$$

Here, n is a refractive index of a medium and α is an angular aperture. The shorter the wavelength is, the lower extent of the resolution becomes and the higher the resolution is. The optical microscope has a resolution of at most 0.1 μm even in use of a shortest wavelength of about 200 nm. That is, the conventional optical system may manipulate only a far field within a cutoff frequency. When a phase of each wave vector within the cutoff frequency reaches a target spot, a focus with limited diffraction having a width of a half wavelength may be acquired. That is, incident light 311 passes through a scattering layer 321 to form a limited focus on the target spot.

Referring to FIG. 3B, when a plane wave enters any scattering layer, a wavelength is scattered and changed into different wavelengths including speckle and evanescent forms. Each wave vector having randomly mixed phases appears as speckles 332 including a sub-wavelength space mode. That is, in a scattering process, even though light 312 having a specific spatial frequency value enters a scattering layer first, resulting spatial frequency components of the light spread in an entire region of a spatial frequency.

Referring to FIG. 3C, when a wavefront acting on a target location is modulated, a resulting wave vector may cause constructive interference so as to form a sub-wavelength focus at the target location. That is, the wavefront is manipulated to manipulate a near field through scattering, thereby forming an ultrahigh-resolution focus at a random location. That is, the present invention may adjust a low spatial frequency component of incident light 313 using scattering, thereby manipulating a high spatial frequency component of light, which is not modulated by the conventional optical system. Thus, the incident light 313 with the wavefront modulated by a basic unit of light may pass through a scattering layer 323 to form an ultrahigh-resolution focus 333 at a target spot.

Figure 4:
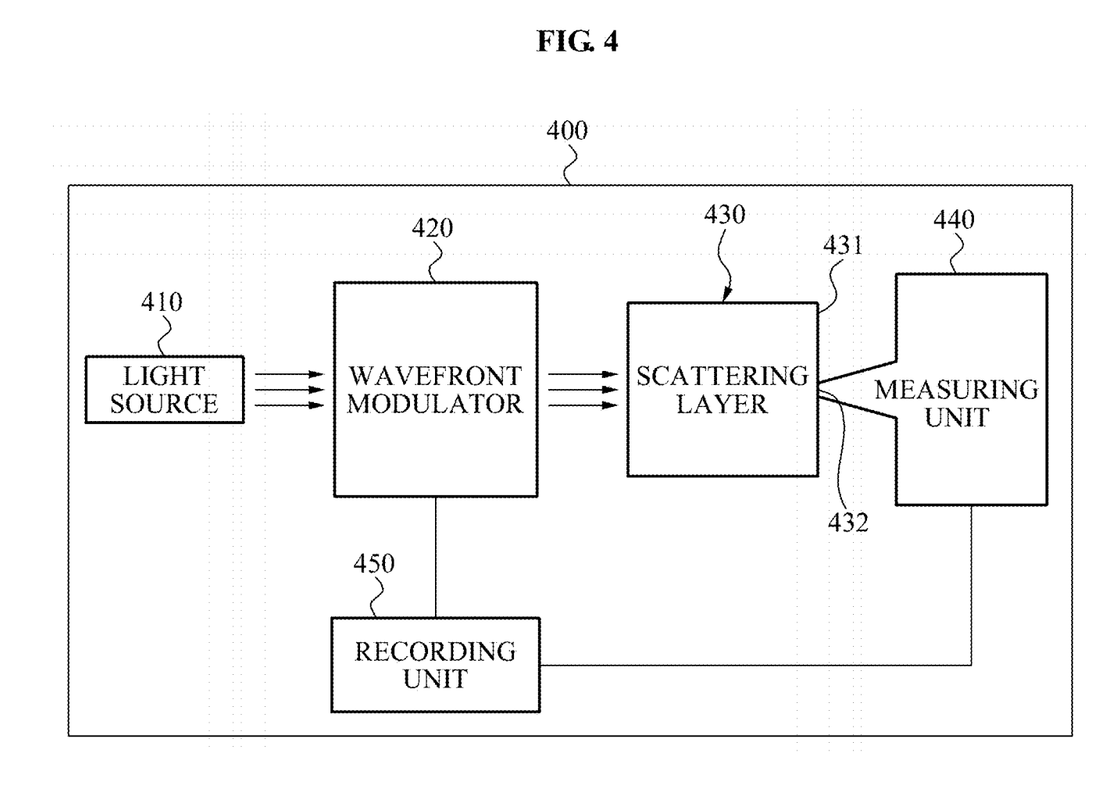
FIG. 4 illustrates a configuration of an apparatus for manipulating a near field using light scattering according to an exemplary embodiment.

FIG. 4 illustrates a configuration of an apparatus for manipulating a near field using light scattering according to an exemplary embodiment.

Referring to FIG. 4, the apparatus 400 for manipulating the near field (also referred to as a "near field manipulating apparatus") according to the present embodiment may include a wavefront modulator 420, a scattering layer 430 and a measuring unit 440.

Here, the wavefront modulator may be a device for manipulating a phase of light or a film with a fixed shape capable of manipulating the phase. For example, the wavefront modulator may include one of a spatial light modulator, a deformable mirror device, a dynamic mirror device, a photorefractive material and a holographic phase film.

In an operation process according to a path of proceeding light, the wavefront modulator 420 may manipulate a phase of light emitted from a coherent light source 410, such as a laser. Here, the light source 410 may include a light source of a visible spectrum. Although plasmonics using resonance phenomena and a near-field scanning optical microscope (NSOM) using a zero-mode waveguide have restrictive conditions of wavelengths, the present embodiment may be applied to all range of wavelengths such as visible rays, infrared rays and microwaves.

According to one exemplary embodiment, the wavefront modulator 420 may manipulate a wavefront of light. The wavefront modulator 420 may set a basic unit to represent a kind of an incident wavefront and change a phase of the light so that constructive interference occurs at a target spot with respect to each basic unit. In one exemplary embodiment, the basic unit may be each spatial frequency. Alternatively, the basic unit may be a pixel.

The light with the manipulated phase or manipulated wavefront may pass through the scattering layer 430. According to one exemplary embodiment, the light with the manipulated phase or manipulated wavefront may form an ultrahigh-resolution focus on a target sample 432 disposed in an inside or rear side of the scattering layer 430.

A near field of the light passing through the scattering layer 430 may be measured by the measuring unit 440 on a surface 431 of the scattering layer 430 that the light exits from. In one exemplary embodiment, the measuring unit 440 may include an NSOM, a structure having an opening with a smaller size than a diffraction limit, a light emitter having a smaller size than the diffraction limit or a probe having a vertex with a smaller size than the Abbe's diffraction limit. The NSOM is a microscopy technique for measurement that breaks the far field resolution limit by exploiting properties of evanescent waves. The NSOM allows for measurement with high spatial and temporal resolution. Here, intensity of the light in a region smaller than the Abbe's diffraction limit may be measured in the near field.

According to an operation process of the near field manipulating apparatus 400, the wavefront modulator 420 of the near field manipulating apparatus 400 may manipulate a phase of light emitted from the coherent light source 410, such as a laser. In one exemplary embodiment, the wavefront modulator 420 may manipulate a wavefront of light. For example, the wavefront modulator 420 may include one of a spatial light modulator, a deformable mirror device, a dynamic mirror device, a photorefractive material and a holographic phase film.

The light with the manipulated phase or manipulated wavefront passes through the scattering unit 430. In one exemplary embodiment, the scattering layer 430 may be formed by using any complex scattering structure of particles or forms having a smaller size than a wavelength of the light. For example, the scattering layer 430 may be formed using ZnO nanoparticles or spray paint.

The measuring unit 440 may measure a near field with respect to the light passing through the scattering layer 430 on the surface 431 of the scattering layer 430 that the light exits from. In one exemplary embodiment, the measuring unit 440 may employ an instrument using an opening or probe capable of measuring a smaller size of light than the Abbe's diffraction limit. For example, the measuring unit 440 may include an NSOM, a structure having an opening with a smaller size than a diffraction limit, a light emitter having a smaller size than the diffraction limit or a probe having a vertex with a smaller size than the Abbe's diffraction limit. Here, intensity of the light in a region smaller than the Abbe's diffraction limit may be measured in the near field.

In one exemplary embodiment, the near field manipulating apparatus 400 may further include a recording unit 450. The recording unit 450 may record a phase with respect to a basic unit of each wavefront forming constructive interference at a target spot of the scattering layer 430 based on the intensity of the light measured by the measuring unit 440. In detail, the recording unit 450 may measure and record a phase of incident light which causes constructive interference at the target spot 432 by conducting feedback based on the intensity of the light measured by the measuring unit 440 and by modulating a wavefront of the light with respect to the basic unit by the wavefront modulator. Accordingly, an optimal wavefront or phase of each basic unit of the incident light is recorded through the feedback and the basic units are superimposed to enter the scattering layer, thereby obtaining desired polarized light at a target spot. Here, information on an optimal phase is recorded for each spot requiring an optical focus and a proper phase is allocated to each spatial frequency, thereby forming optical focuses on random spots.

Figure 5:
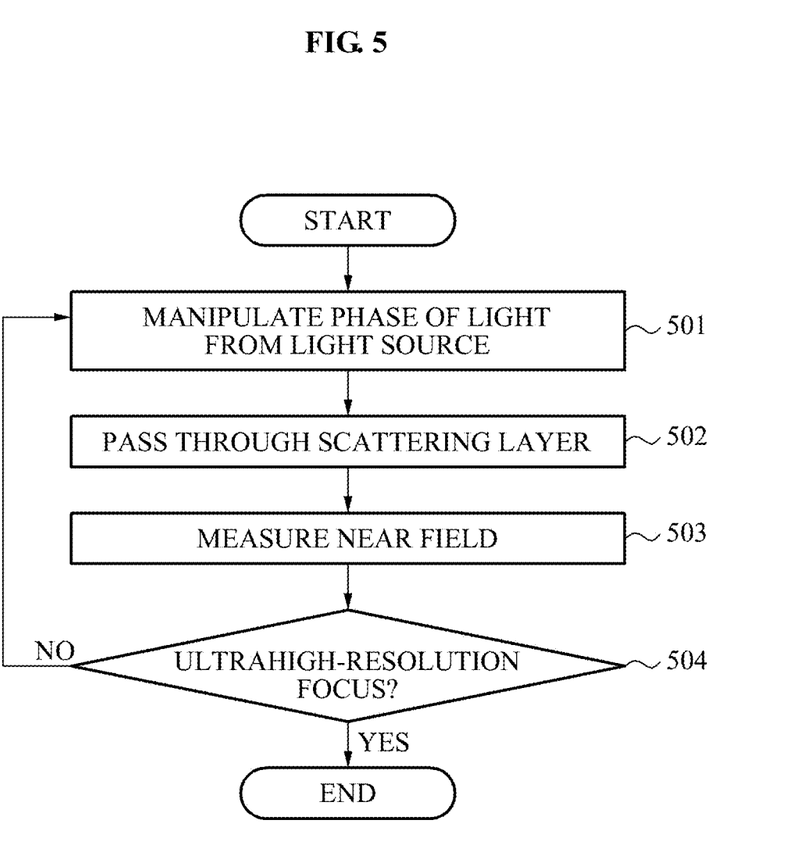
FIG. 5 is a flowchart illustrating a method of manipulating a near field through feedback using light scattering according to an exemplary embodiment.

FIG. 5 is a flowchart illustrating a method of manipulating a near field through feedback using light scattering according to an exemplary embodiment.

FIG. 5 provides the method of manipulating the near field using light scattering according to the exemplary embodiment. In operation 501, a phase of light from a coherent light source is manipulated by a wavefront modulator. For example, light emitted from a coherent light source, such as a laser, may enter the wavefront modulator. The light source may include a visible-spectrum light source. Here, the wavefront modulator may manipulate a phase of the light by a basic unit. Alternatively, the wavefront modulator may manipulate a wavefront of the light by a basic unit. Here, the basic unit may be a pixel.

In operation 502, the light with the manipulated phase is passed through a scattering layer. For example, the scattering layer through which the light with the manipulated phase passes may include ZnO nanoparticles or spray paint.

In operation 503, intensity of the light is measured in a near field of a surface that the light passing through the scattering layer exits from. For example, the near field of the surface that the light exits from may be a near field of a target spot. Here, the target spot may be a location on which an optical focus is to be formed. In one exemplary embodiment, the near field may be measured by either of an NSOM and a quantum dot measuring apparatus.

In one exemplary embodiment, a basic unit to represent a type of an incident wavefront may be set. For instance, each spatial frequency may be set as the basic unit. Next, a phase of each basic unit to cause constructive interference at a target spot, for example, a spot for forming a focus, may be measured.

In operation 504, it is determined whether an ultrahigh-resolution focus is formed at a desired location. For instance, it may be determined whether the ultrahigh-resolution focus is formed by determining whether the intensity of the light in the near field measured after changing the phase of the basic unit of the light is higher than that measured before changing the phase of the basic unit of the light. Alternatively, it may be determined that the ultrahigh-resolution focus is formed at the location in which the phase of the light has a focus having highest resolution by changing the phase of each basic unit of the light. Also, it may be determined whether the ultrahigh-resolution focus is formed by determining whether the light is formed of spatial frequency components beyond the Abbe's diffraction limit. Due to the Abbe's diffraction limit, a microscope has a resolution of at most 0.2 µm even in use of a shortest wavelength of visible light, and such resolution allows a clear observation of an object magnified at most 3,000 times, enabling only a vague observation of an object magnified over the magnification despite mixing and matching with any lens.

When the ultrahigh-resolution focus is not formed at the desired location in operation 504, operation 501 is repeated. In this case, in operation 501, the wavefront modulator changes the phase of the light based on a result of measurement by the measuring apparatus. For example, the wavefront modulator changes the phase of the light by a basic unit of incident light to the wavefront modulator to cause constructive interference at a target spot. Operation 501 may further include retrieving a phase to cause constructive interference by changing a phase of each basic unit of incident light to the wavefront modulator using the wavefront modulator, and recording the phase to cause constructive interference. In detail, the phase of the basic unit to cause constructive interference may be found by changing the phase of each basic unit of the incident light with the wavefront modulator based on the measurement result by the measuring apparatus. The basic units are superimposed at the target spot, thereby forming a ultrahigh-resolution focus. When the phases of the basic units to cause constructive interference are recorded and stored, the incident wavefront may be adjusted in real time in a lithography process, thereby simultaneously forming or moving ultrahigh-resolution optical focuses at a plurality of spots.

According to one exemplary embodiment, operations 501 to 504 may be repeated until an ultrahigh-resolution focus is formed at a desired location. For example, changing the phase of the light by the wavefront modulator in operation 501, measuring the near field of the light passing through the scattering layer in operation 503 and determining whether an ultrahigh-resolution focus is formed at a desired location in operation 504 may be carried out until the ultrahigh-resolution focus is formed at the desired location.

In one exemplary embodiment, measuring the intensity of the light at the desired focus location, that is, the target location, and feeding back the measurement may be carried out successively.

When the ultrahigh-resolution focus is formed at the desired location in operation 504, the method of manipulating the near field using light scattering is complete. An optimal wavefront for each basic unit is recorded through the feedback and the basic units are superimposed to enter the scattering layer, thereby obtaining desired polarized light at the target spot. Information on an optimal phase is recorded for each spot requiring an optical focus through the feedback and a proper phase is allocated to each spatial frequency, thereby forming optical focuses on random spots. According to one exemplary embodiment, spatial frequency components adjustable by the wavefront modulator are determined by the Abbe's diffraction limit, while resultant spatial frequency components from passing through the scattering layer include a plurality of components beyond the limit.

Figure 6:
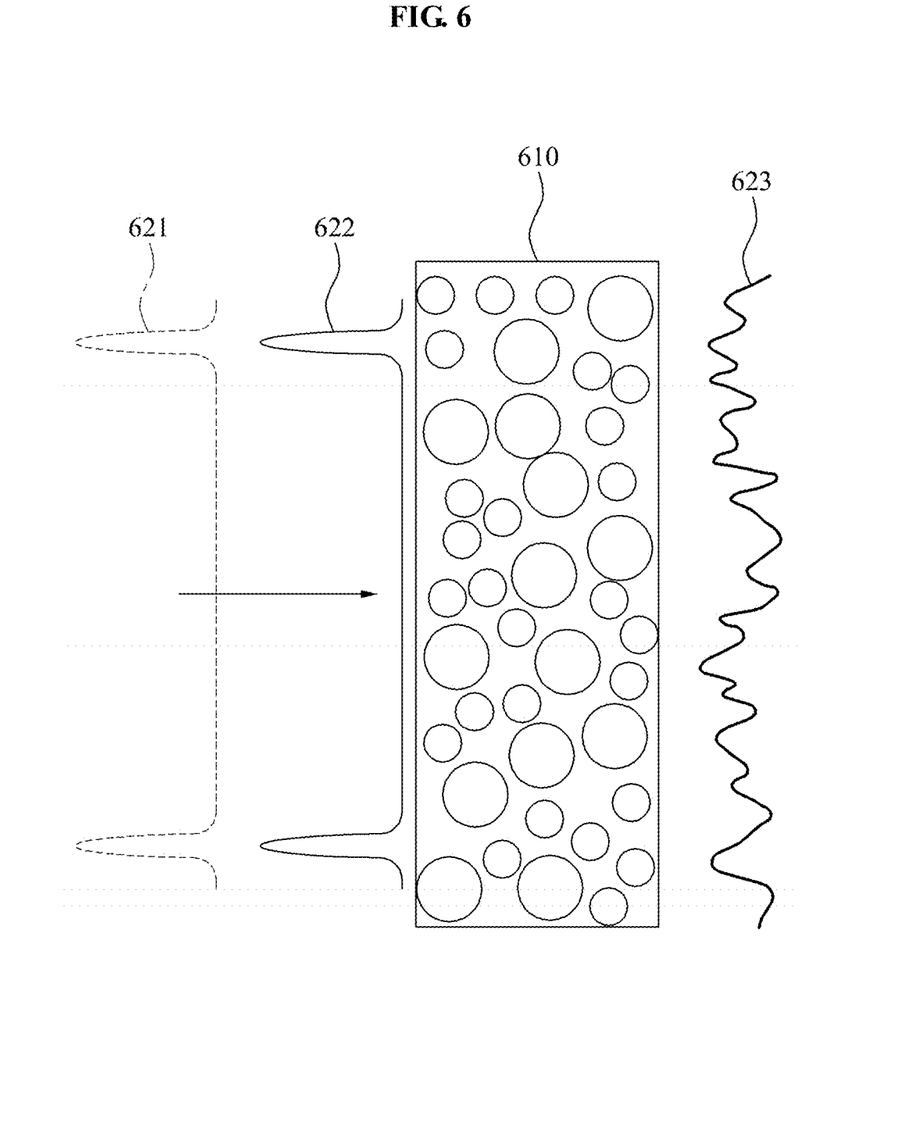
FIG. 6 illustrates conversion of a near field entering a scattering layer into a far field via the scattering layer.

FIG. 6 illustrates conversion of a near field entering a scattering layer into a far field via the scattering layer.

Generally, when there is no own movement of the scattering layer, a pattern of speckles formed when a specific pattern of light enters the scattering layer is always uniform. That is, each speckle pattern may correspond to each specific wavefront of the incident light. Near-field imaging may be realized using such characteristics.

A pattern of speckles formed after a particular incident wavefront passes through the scattering layer is always uniform. When this incident wavefront is spatially broken down, a two-dimensional plane of the incident wavefront may be expressed with a great number of dots. Here, if information on the speckles corresponding to the respective dots in the space is measured, a random incident wavefront may be reconstructed based on the information on the speckles generated when the random incident wavefront passes through the scattering layer. Here, since the speckles are generated by interference of coherent light, a phase of the pattern of the speckles may need considering in measuring the information on the speckles so as to reconstruct an exact image.

In a method of measuring a near-field image using light scattering, a near field, which decays exponentially with progress, is converted into a far field which is able to travel to long distance after passing through the scattering layer. Using this property, even information on a near field around an object to be inspected may be obtained even with a general far-field optical microscope.

Referring to FIG. 6, a near field 622 of a high spatial frequency component may be scattered by a scattering layer 610 and transformed into a far field 623 of a low spatial frequency component which can be measured by a general optical system. When a wavefront 622 including the near field enters the scattering layer 620, the wavefront 622 may be converted into a far field 623 including a plurality of spatial frequencies via scattering. Here, the far field 623 may appear as speckles on an opposite side of the scattering layer.

Figure 7:
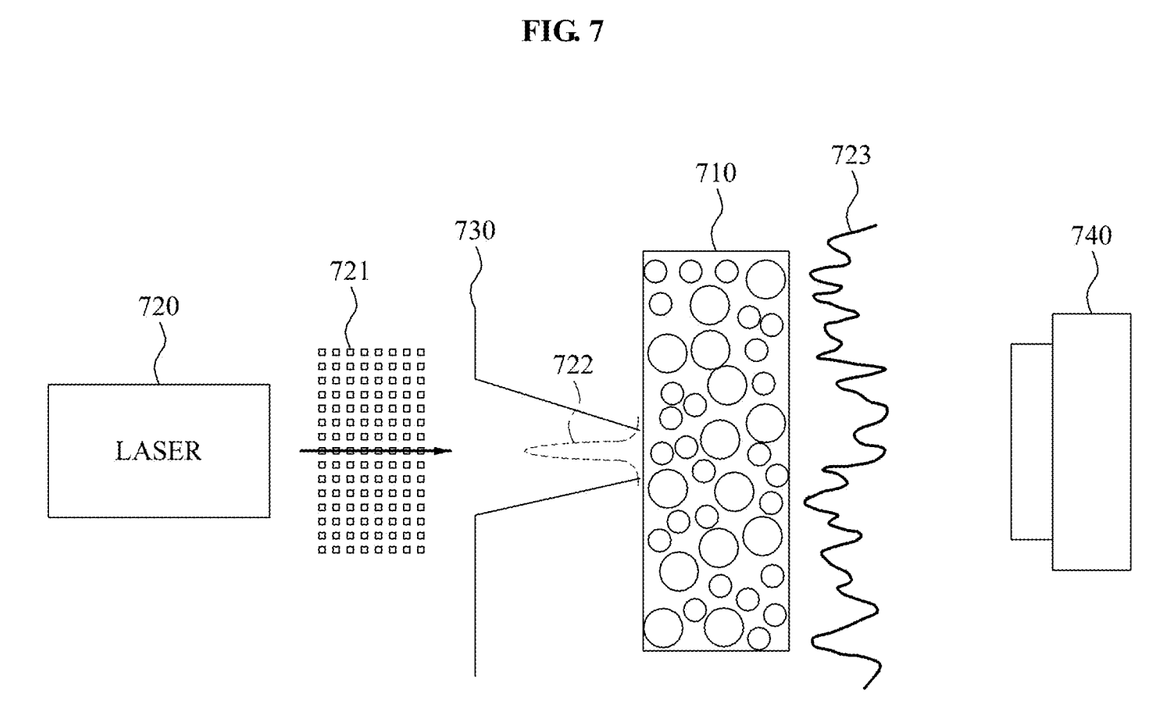
FIG. 7 illustrates an apparatus for measuring speckle information per input basis with respect to the scattering layer according to an exemplary embodiment.

FIG. 7 illustrates an apparatus for measuring speckle information per input basis with respect to a scattering layer according to an exemplary embodiment.

FIG. 7 illustrates the apparatus for measuring the speckle information on the scattering layer according to a path of light. A measuring unit 740 may measure information on speckles 723 generated when an incident wavefront 721 emitted from a coherent light source 720 such as a laser passes through a structure 730 to form an input basis and light 722 passing through the structure 730 passes through the scattering layer 710. The measuring unit 740 may acquire pattern information on the speckles using a general microscope and measure phases of the speckles using a holographic measuring unit. The structure 730 may pass the light 721 from the coherent light source 720 to form the light 722 of an input basis. Here, the structure 730 may be at least one of an NSOM tip, a metallic probe and a plasmonic metastructure which are capable of spatially breaking down each wavefront. The speckles generated at locations on an entire surface of the scattering layer may be measured while moving the structure 730 to form the input basis. A sample is placed on the scattering layer, involved in measuring the information on the speckles, and a plane wave is passed through the sample, thereby acquiring an image of the sample. That is, after scattering information on the scattering layer is completely measured, the scattering layer may be used as an ultrahigh-resolution imaging device.

In one exemplary embodiment, speckle information on a plurality of input bases may be acquired by measuring speckle information at each location of the input basis while changing locations on the scattering layer that the light of the input bases formed by the structure 730 passes through. Here, a process of measuring the speckle information at each location of the input basis for measuring the scattering information on the scattering layer may involve sequential scanning of an entire area of the scattering layer. Alternatively, the speckle pattern may need to be measured a plurality of times. This measuring process is a preliminary to conducting actual imaging, and is not repeated once the speckle information on the scattering layer at each location of the input basis is measured. In one exemplary embodiment, once the speckle information on the scattering layer at each location of the input basis is recorded, a sample to be measured is placed on the scattering layer and speckles are measured in only one sheet, thereby acquiring an image of an entire area of the sample at a time by ultrahigh-resolution imaging. Here, since measurable size of the sample includes the entire region covered by the input basis involved in measuring the information on the scattering layer, and thus large-area ultrahigh-resolution imaging may be realized in real time.

Figure 8:
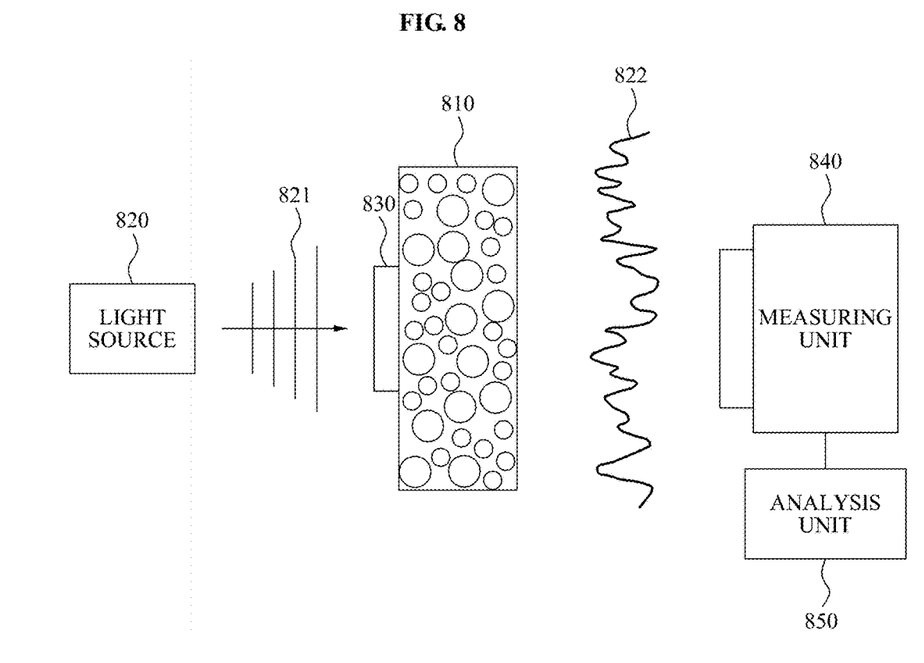
FIG. 8 illustrates an apparatus for acquiring speckle information on a sample and the scattering layer to obtain an image of the sample according to an exemplary embodiment.

FIG. 8 illustrates an apparatus for acquiring speckle information on a sample and a scattering layer to obtain an image of the sample according to an exemplary embodiment.

Referring to FIG. 8, a sample 830 to be imaged is placed on a surface of a scattering layer 810, on which speckles generated per input basis are measured, and a plane wave 821 emitted from a light source 820 is passed through the scattering layer 810, after which generated speckles 822 are measured by a measuring unit 840. Here, correlation between the measured speckles and the speckles per input basis measured in advance is calculated, and a correlation value is used as an image of the sample 830. That is, information on the speckles 822 generated with the sample placed may be analyzed with information on the speckles per input basis. Here, since the speckles generated with the sample placed has a size expressed within the diffraction limit but includes a far field component converted from a near field component of the sample 830, ultrahigh-resolution imaging is possible.

Unlike a conventional NSOM and plasmonics using a near field, the apparatus does not limit size of an opening that allows light to physically pass through or not use a metallic metastructure of resonance, and thus enables dynamic observations of living cells and reduces measurement time. Further, a high spatial frequency component of light including high-resolution information on the sample 830 to be measured may be scattered by the scattering layer and transformed into a low spatial frequency component of light 822 measured by a general optical system.

According to one exemplary embodiment, a near-field imaging apparatus may include a light source to output a plane wave, a scattering layer on which a sample to be imaged is disposed, a measuring unit to acquire speckle information on a speckle generated by the plane wave passing through the sample and the scattering layer, and an analysis unit 850 to analyze the speckle information. The light source to output the plane wave may include a coherent light source. The measuring unit may include a general microscope to acquire a pattern of the speckle and a holographic measuring unit to acquire a phase of the speckle. The analysis unit 850 calculates correlation between the speckle information and speckle information per input basis about the scattering layer measured in advance and determines similarity therebetween using the correlation, thereby acquiring an image of the sample.

Figure 9:
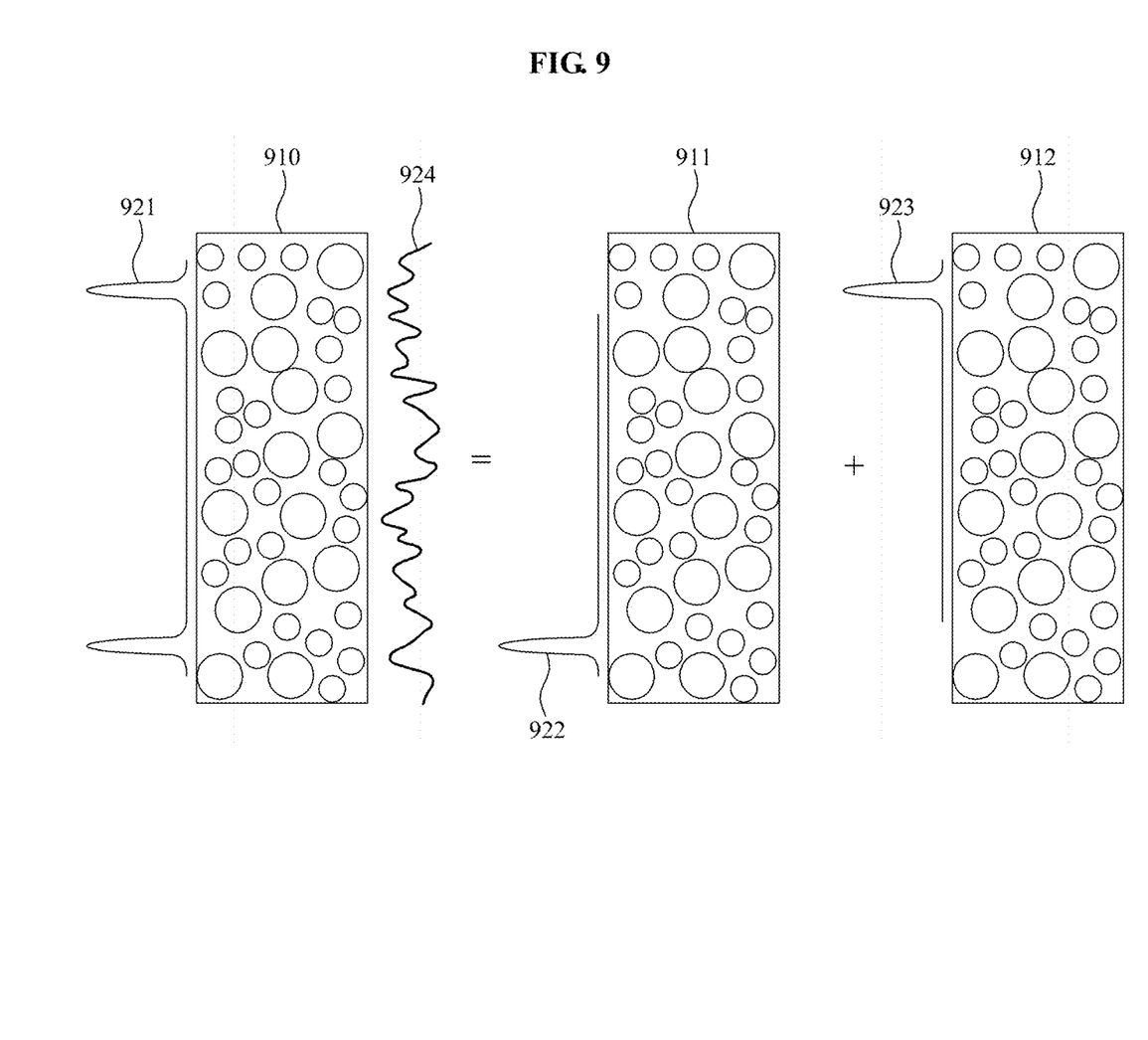
FIG. 9 illustrates a method of realizing near-field imaging of the sample through the speckle information on the scattering layer according to an exemplary embodiment.

FIG. 9 illustrates a method of realizing near-field imaging of a sample through speckle information on a scattering layer according to an exemplary embodiment.

An image of a sample may be acquired through the analysis unit of the near-field imaging apparatus. First, correlation between speckle information per input basis about the scattering layer measured in advance and speckle information 924 on the scattering layer which the sample is attached to is calculated to determine similarity therebetween, and the image of the sample is acquired using the correlation. Generally, when there is no own movement of the scattering layer, a pattern of speckles formed when a specific pattern of light enters the scattering layer is always uniform. That is, each speckle pattern may correspond to each specific wavefront of the incident light. Near-field imaging may be realized using such characteristics.

Referring to FIG. 9, a combination of speckle information on the scattering layer 911 at a first location 922 of an input basis and speckle information on the scattering layer 912 at a second location 923 of an input basis may be speckle information acquired after a plane wave enters the scattering layer 910 that the sample is attached to. The scattering layer 910, the scattering layer 911 and the scattering layer 912 are the same scattering layer. A near-field image of the sample may be acquired by analyzing the speckle information 924 obtained from the scattering layer that the sample is attached to. The speckle information 924 may be a combination of the speckle information on the scattering layer at the first location 922 of the input basis and the speckle information on the scattering layer at the second location 923 of the input basis. Here, the near-field image of the sample may be an input 921 obtained by combining the first position and the second location of the input basis.

In analysis of the speckle information 924, correlation between the speckle information obtained from the scattering layer that the sample is attached to and speckle information per input basis on the scattering layer measured in advance may be calculated, and the image of the sample may be obtained using the correlation. Here, when the correlation between the speckle information obtained from the scattering layer that the sample is attached to and the speckle information per input basis on the scattering layer measured in advance is calculated, a correlation value may be the near-field image of the sample. Here, since the speckle information obtained from the scattering layer that the sample is attached to has a size expressed within the diffraction limit but includes a far field component converted from a near field component of the sample, ultrahigh-resolution imaging is possible.

Figure 10:
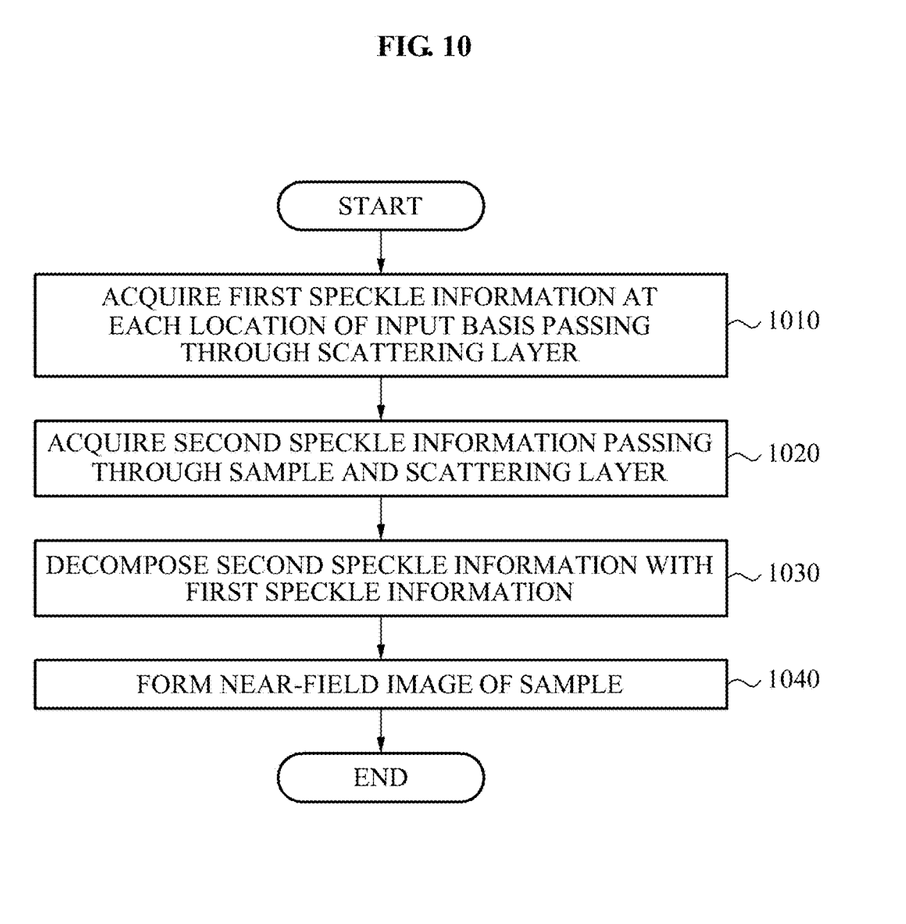
FIG. 10 is a flowchart illustrating a method of realizing near-field imaging of the sample using light scattering according to an exemplary embodiment.

FIG. 10 is a flowchart illustrating a method of realizing near-field imaging of a sample using light scattering according to an exemplary embodiment. FIG. 10 shows the method of realizing near-field imaging of the sample using a scattering layer. The method of realizing near-field imaging may include acquiring first speckle information on a speckle generated by light from a coherent light source passing through the scattering layer, acquiring second speckle information on a speckle generated by a plane wave passing through a sample and the scattering layer, and acquiring an image of the sample using the first speckle information and the second speckle information. Here, the coherent light source may be a laser.

In operation 1010, the acquiring of the first speckle information may be acquiring speckle information on the scattering layer at each location of an input basis. In detail, the acquiring of the first speckle information may include forming light of an input basis by passing the light from the coherent light source through a structure, passing the light of the input basis through the scattering layer to be scattered, and acquiring input basis speckle information on a speckle generated by the scattered light. Here, the structure may include at least one of an NSOM tip, a metallic probe and a plasmonic metastructure which are capable of spatially breaking down each wavefront. According to one exemplary embodiment, speckles generated at each location on the entire surface of the scattering layer may be measured by repeating the forming of the light, the passing of the light and the acquiring of the input basis speckle information while moving the structure to form the input basis. Operation 1010 of the acquiring of the first speckle information is a preliminary to conducting actual imaging, and is not repeated once the speckle information on the scattering layer at each location of the input basis is measured.

In operation 1020, the acquiring of the second speckle information may include attaching a sample to the scattering layer involved in acquiring the first speckle information, and acquiring speckle information created by the plane wave entering. Here, the speckle information may include a pattern of the speckle acquired by a general microscope and a phase of the speckle acquired by a holographic measuring unit. According to one exemplary embodiment, the sample to be imaged is placed on the scattering layer involved in measuring the speckle information and a plane wave is passed through the sample, thereby acquiring a near-field image of the sample. That is, after the first speckle information on the scattering layer is completely measured, the scattering layer may be used as an ultrahigh-resolution imaging device.

In operation 1030, the second speckle information acquired from the scattering layer that the sample is attached to may be analyzed with the first speckle information at each location of the input basis prepared in advance. According to one exemplary embodiment, the image of the sample may be acquired through the analysis unit of the near-field imaging apparatus. Generally, when there is no own movement of the scattering layer, a pattern of speckles formed when a specific pattern of light enters the scattering layer is always uniform. That is, each speckle pattern may correspond to each specific wavefront of the incident light. Near-field imaging may be realized using such characteristics. A combination of speckle information on the scattering layer at a first location of the input basis and speckle information on the scattering layer at a second location of the input basis may be speckle information acquired after the plane wave enters the scattering layer that the sample is attached to. A near-field image of the sample may be acquired by analyzing the speckle information obtained from the scattering layer that the sample is attached to. The speckle information obtained from the scattering layer that the sample is attached to may be a combination of the speckle information on the scattering layer at the first location of the input basis and the speckle information on the scattering layer at the second location of the input basis. Here, the near-field image of the sample may be an input obtained by combining the first position and the second location of the input basis.

In operation 1040, the near-field image of the sample may be acquired through the information decomposed in operation 1030. According to one exemplary embodiment, the image of the sample may be acquired by calculating correlation between the speckle information obtained from the scattering layer that the sample is attached to and speckle information per input basis on the scattering layer acquired in advance and by determining similarity therebetween using the correlation. Here, in analysis of the speckle information obtained from the scattering layer that the sample is attached to, the correlation between the speckle information obtained from the scattering layer that the sample is attached to and the speckle information per input basis on the scattering layer measured in advance may be calculated and the image of the sample may be obtained using the correlation. Here, when the correlation between the speckle information obtained from the scattering layer that the sample is attached to and the speckle information per input basis on the scattering layer measured in advance is calculated, a correlation value may be the near-field image of the sample.

As described above, once the speckle information on the scattering layer at each location of the input basis is recorded, a sample to be measured is placed on the scattering layer and speckles are measured in only one sheet, thereby acquiring an image of an entire area of the sample at a time by ultrahigh-resolution imaging. Here, since measurable size of the sample includes the entire region covered by the input basis involved in measuring the information on the scattering layer, and thus large-area ultrahigh-resolution imaging may be realized in real time.

While a few exemplary embodiments have been shown and described with reference to the accompanying drawings, it will be apparent to those skilled in the art that various modifications and variations can be made from the foregoing descriptions. For example, adequate effects may be achieved even if the foregoing processes and methods are carried out in different order than described above, and/or the aforementioned elements, such as systems, structures, devices, or circuits, are combined or coupled in different forms and modes than as described above or be substituted or switched with other components or equivalents.

Thus, other implementations, alternative embodiments and equivalents to the claimed subject matter are construed as being within the appended claims.

What is claimed is:

1. A near-field imaging apparatus comprising:
   a light source to output a plane wave;
   a scattering layer on which a sample to be imaged is disposed;
   a measuring unit to acquire speckle information on a speckle generated by the plane wave passing through the sample and the scattering layer; and
   an analysis unit to analyze the speckle information,
   wherein the measuring unit comprises at least one of a general microscope or a holographic measuring unit, and
   wherein the analysis unit calculates correlation between the speckle information and speckle information per input basis about the scattering layer and acquires an image of the sample using the correlation.

2. The near-field imaging apparatus of claim 1, wherein the holographic measuring unit acquires a phase of the speckle.

3. The near-field imaging apparatus of claim 1, further comprising a structure to pass light from a coherent light source to form light of the input basis.

4. The near-field imaging apparatus of claim 3, wherein the structure comprises at least one of a near-field scanning optical microscope (NSOM) tip, a metallic probe and a plasmonic metastructure.

5. The near-field imaging apparatus of claim 3, wherein the scattering layer passes the light of the input basis, formed by passing through the structure, to be scattered in the absence of the sample, and the measuring unit acquires input basis speckle information on a speckle generated by the scattered light.

6. A method of realizing near-field imaging, the method comprising:
   acquiring first speckle information on a speckle generated by light from a coherent light source passing through a scattering layer;
   acquiring second speckle information on a speckle generated by a plane wave passing through a sample and the scattering layer; and
   acquiring an image of the sample using the first speckle information and the second speckle information,
   wherein the acquiring of the image of the sample using the first speckle information and the second speckle information comprises calculating correlation between the first speckle information and the second speckle information and acquiring the image of the sample using the correlation.

7. The method of claim 6, wherein the acquiring of the first speckle information comprises forming light of an input basis by passing the light from the coherent light source through a structure, passing the light of the input basis through the scattering layer to be scattered, and acquiring input basis speckle information on a speckle generated by the scattered light.

8. The method of claim 7, wherein the acquiring of the first speckle information comprises acquiring a plurality of input basis speckle informations by conducting the forming of the light, the passing of the light and the acquiring of the input basis speckle information while changing a location on the scattering layer that the light of the input basis passes through, and acquiring the first speckle information using the plurality of input basis speckle informations.

9. The method of claim 7, wherein the structure comprises at least one of a near-field scanning optical microscope (NSOM) tip, a metallic probe and a plasmonic metastructure.

* * * * *